(12) United States Patent
Goel et al.

(10) Patent No.: US 10,789,855 B2
(45) Date of Patent: Sep. 29, 2020

(54) FITNESS DEVICE CONFIGURED TO PROVIDE GOAL MOTIVATION

(71) Applicant: NIKE, Inc., Beaverton, OR (US)

(72) Inventors: Manan Goel, Beaverton, OR (US); Christopher L. Andon, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 656 days.

(21) Appl. No.: 14/513,398

(22) Filed: Oct. 14, 2014

(65) Prior Publication Data

US 2015/0104772 A1 Apr. 16, 2015

Related U.S. Application Data

(60) Provisional application No. 61/890,719, filed on Oct. 14, 2013.

(51) Int. Cl.
| | |
|---|---|
| *A61B 5/11* | (2006.01) |
| *G09B 5/02* | (2006.01) |
| *A63B 71/06* | (2006.01) |
| *A61B 5/00* | (2006.01) |
| *A61B 5/22* | (2006.01) |

(52) U.S. Cl.
CPC .............. *G09B 5/02* (2013.01); *A61B 5/1112* (2013.01); *A61B 5/1118* (2013.01); *A61B 5/221* (2013.01); *A61B 5/486* (2013.01); *A61B 5/681* (2013.01); *A63B 71/06* (2013.01); *A61B 5/742* (2013.01); *A61B 5/7405* (2013.01); *A61B 5/7455* (2013.01); *A61B 2562/0219* (2013.01)

(58) Field of Classification Search
CPC ....... G09B 19/003; G09B 5/02; A61B 5/1112; A61B 5/1118; A61B 5/221; A61B 5/486; A61B 5/681; A61B 5/7405; A61B 5/742; A61B 5/7455; A61B 2562/0219; A63B 71/06
USPC ......................................................... 434/238
See application file for complete search history.

(56) References Cited

U.S. PATENT DOCUMENTS

| | | | |
|---|---|---|---|
| 2008/0214360 A1* | 9/2008 | Stirling ................ | A61B 5/1038 482/9 |
| 2012/0071731 A1* | 3/2012 | Gottesman ........... | A61B 5/6833 600/301 |
| 2013/0138734 A1* | 5/2013 | Crivello ............... | G09B 19/003 709/204 |
| 2013/0191034 A1* | 7/2013 | Weast ..................... | G06F 17/00 702/19 |

FOREIGN PATENT DOCUMENTS

| | | |
|---|---|---|
| JP | H08126632 A | 5/1996 |
| JP | 2002306660 A | 10/2002 |

(Continued)

OTHER PUBLICATIONS

Feb. 6, 2015—(WO) ISR and WO—App. No. PCT/US2014/060359.

*Primary Examiner* — Robert P Bullington
(74) *Attorney, Agent, or Firm* — Banner & Witcoff, Ltd.

(57) ABSTRACT

A system configured to provide feedback to a user in order to motivate said user to reach one or more energy expenditure goals. The one or more energy expenditure goals may be associated with one or more of time periods, or activity sessions, and the feedback may be provided to a user using one or more of a visual display on a sensor device worn by a user, and/or using audible and haptic feedback.

18 Claims, 7 Drawing Sheets

(56) References Cited

FOREIGN PATENT DOCUMENTS

| | | | |
|---|---|---|---|
| JP | 2004318503 | A | 11/2004 |
| JP | 2007164623 | A | 6/2007 |
| JP | 2013172757 | A | 9/2013 |
| JP | 2015503993 | A | 2/2015 |
| KR | 20130111569 | A | 10/2013 |
| WO | 20120614.38 | A2 | 5/2012 |

* cited by examiner

FITNESS DEVICE CONFIGURED TO PROVIDE GOAL MOTIVATION

CROSS-REFERENCE TO RELATED APPLICATION

This application claims priority to U.S. Provisional Patent Application No. 61/890,719, entitled "FITNESS DEVICE CONFIGURED TO PROVIDE GOAL MOTIVATION," filed on Oct. 14, 2013, which is expressly incorporated herein by reference in its entirety for any and all non-limiting purposes.

BACKGROUND

Modern technology has given rise to a wide variety of different electronic and/or communication devices that keep users in touch with one another, entertained, and informed. A wide variety of portable electronic devices are available for these purposes, such as: cellular telephones; personal digital assistants ("PDAs"); pagers; beepers; MP3 or other audio playback devices; radios; portable televisions, DVD players, or other video playing devices; watches; GPS systems; etc. Many people like to carry one or more of these types of devices with them when they exercise and/or participate in athletic events, for example, to keep them in contact with others (e.g., in case of inclement weather, injuries; or emergencies; to contact coaches or trainers; etc.), to keep them entertained, to provide information (time, direction, location, and the like).

Athletic performance monitoring systems also have benefited from recent advancements in electronic device and digital technology. Electronic performance monitoring devices allow for monitoring of many physical or physiological characteristics associated with exercise or other athletic performances, including, for example: speed and distance data, altitude data, GPS data, heart rate, pulse rate, blood pressure data, body temperature, etc. Specifically, these athletic performance monitoring systems have benefited from recent advancements in microprocessor design, allowing increasingly complex computations and processes to be executed by microprocessors of successively diminutive size. These modern microprocessors may be used for execution of activity recognition processes, such that a sport or activity that is being carried out by an athlete can be recognized, and information related to that sport or activity can be analyzed and/or stored.

In some instances, athletic performance monitoring systems may allow a user to set one or more goals associated with athletic activities to be carried out by the user. These one or more goals may be associated with, among others goal energy expenditure values to be achieved throughout a period of time, and the like. In some instances, however, a user may discover that he/she has not met one or more activity goals, but that he/she was within a range of one or more activity goals that could have been met if feedback was provided related to a closeness of a real-time activity value to a goal activity value.

Aspects of this disclosure are directed towards novel systems and methods that address one or more of these deficiencies. Further aspects relate to minimizing other shortcomings in the art.

BRIEF SUMMARY

The following presents a simplified summary of the present disclosure in order to provide a basic understanding of some aspects of the systems and methods described herein. This summary is not an extensive overview of the systems and methods described herein. It is not intended to identify key or critical elements of the systems and methods described herein or to delineate the scope of the systems and methods described herein. The following summary merely presents some concepts of the invention in a simplified form as a prelude to the more detailed description provided below.

In one aspect, this disclosure includes a system configured to provide feedback to a user in order to motivate said user to reach one or more energy expenditure goals. The one or more energy expenditure goals may be associated with one or more of time periods, or activity sessions, and the feedback may be provided to a user using one or more of a visual display on a sensor device worn by a user, and/or using audible and haptic feedback.

In another aspect, this disclosure relates to an apparatus having a processor, and a non-transitory computer-readable medium having instructions that are executed by the processor, causing the apparatus to receive sensor data from an activity sensor associated with the user, calculate an energy expenditure of the user from the received sensor data, and identify an activity session from the received sensor data. The instructions further cause the apparatus to calculate a total energy expenditure for the user during the identified activity session, and communication a message to the user representing a closeness of the calculated total energy expenditure to a goal energy expenditure for the user.

In another aspect, this disclosure relates to a unitary apparatus configured to be worn on an appendage of a user, and having a sensor for capturing acceleration data from the appendage of the user, a processor connected to the sensor, and a non-transitory computer-readable medium with computer-executable instructions that are executed by the processor. The computer-executable instructions include receiving acceleration data from the sensor, calculating an energy expenditure of the user from the received acceleration data, identifying activity session associated with received acceleration data, calculating a total energy expenditure for the user during the activity session, and communicating a message to the user encouraging the user to meet a goal energy expenditure.

In yet another aspect, this disclosure relates to a non-transitory computer-readable medium comprising computer-executable instructions executed by a processor to receive sensor data from an activity sensor on a user, calculate an energy expenditure value for the user from the received sensor data, identify an activity session associated with the received data, calculate a total energy expenditure for the user associated with the identified activity session, and communicate a message encouraging the user to exceed a previous energy expenditure totals for the identified activity session.

DETAILED DESCRIPTION

Aspects of this disclosure involve obtaining, storing, and/or processing athletic data relating to the physical movements of an athlete. The athletic data may be actively or passively sensed and/or stored in one or more non-transitory storage mediums. Still further aspects relate to using athletic data to generate an output, such as for example, calculated athletic attributes, feedback signals to provide guidance, and/or other information. These and other aspects will be discussed in the context of the following illustrative examples of a personal training system.

In the following description of the various embodiments, reference is made to the accompanying drawings, which form a part hereof, and in which is shown by way of illustration various embodiments in which aspects of the disclosure may be practiced. It is to be understood that other embodiments may be utilized and structural and functional modifications may be made without departing from the scope and spirit of the present disclosure. Further, headings within this disclosure should not be considered as limiting aspects of the disclosure and the example embodiments are not limited to the example headings.

I. Example Personal Training System

A. Illustrative Networks

Figure 1:
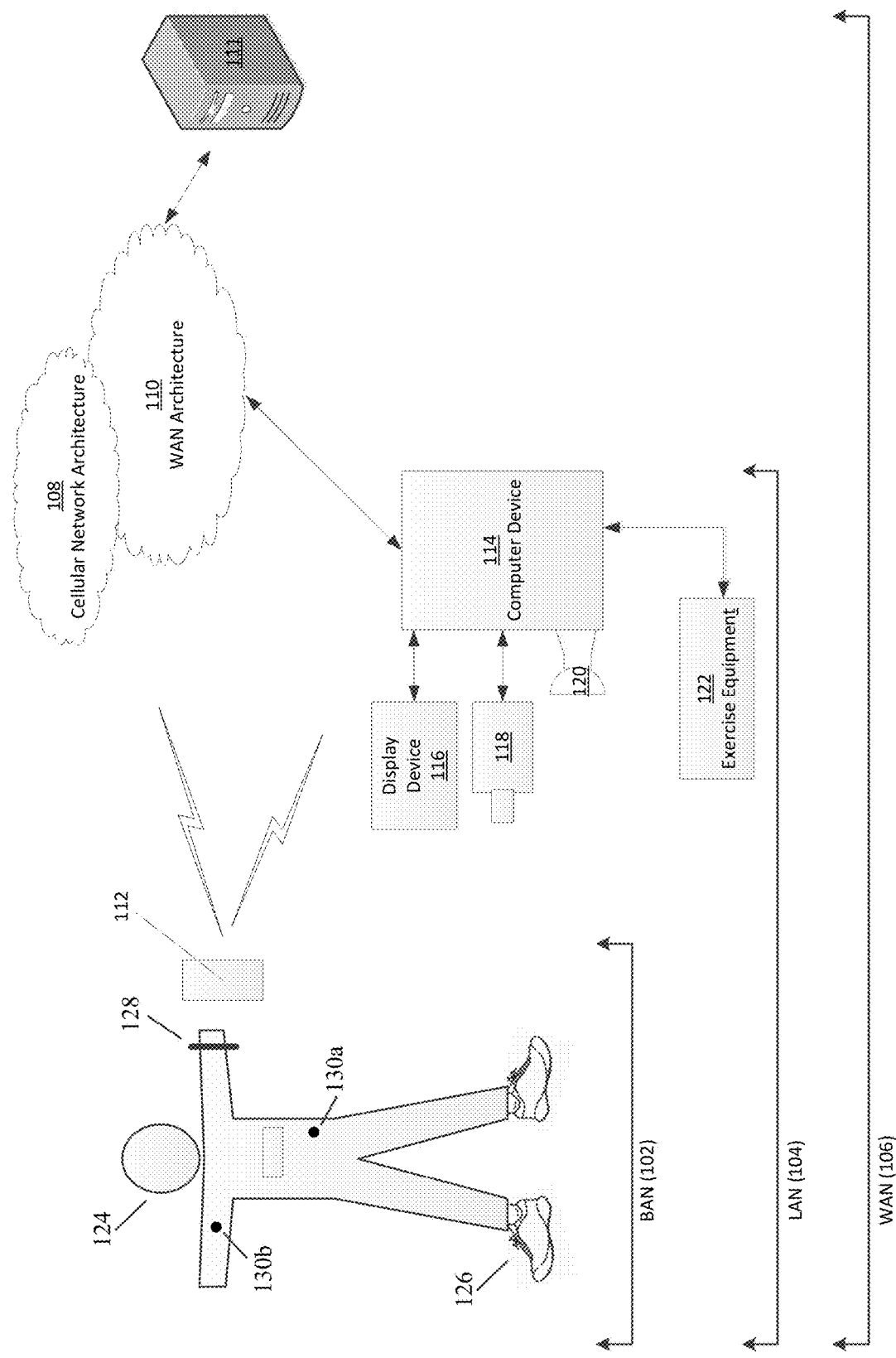
FIG. 1 illustrates an example system that may be configured to provide personal training and/or obtain data from the physical movements of a user in accordance with example embodiments.

Aspects of this disclosure relate to systems and methods that may be utilized across a plurality of networks. In this regard, certain embodiments may be configured to adapt to dynamic network environments. Further embodiments may be operable in differing discrete network environments. FIG. 1 illustrates an example of a personal training system 100 in accordance with example embodiments. Example system 100 may include one or more interconnected networks, such as the illustrative body area network (BAN) 102, local area network (LAN) 104, and wide area network (WAN) 106. As shown in FIG. 1 (and described throughout this disclosure), one or more networks (e.g., BAN 102, LAN 104, and/or WAN 106), may overlap or otherwise be inclusive of each other. Those skilled in the art will appreciate that the illustrative networks 102-106 are logical networks that may each comprise one or more different communication protocols and/or network architectures and yet may be configured to have gateways to each other or other networks. For example, each of BAN 102, LAN 104 and/or WAN 106 may be operatively connected to the same physical network architecture, such as cellular network architecture 108 and/or WAN architecture 110. For example, portable electronic device 112, which may be considered a component of both BAN 102 and LAN 104, may comprise a network adapter or network interface card (NIC) configured to translate data and control signals into and from network messages according to one or more communication protocols, such as the Transmission Control Protocol (TCP), the Internet Protocol (IP), and the User Datagram Protocol (UDP) through one or more of architectures 108 and/or 110. These protocols are well known in the art, and thus will not be discussed here in more detail.

Network architectures 108 and 110 may include one or more information distribution network(s), of any type(s) or topology(s), alone or in combination(s), such as for example, cable, fiber, satellite, telephone, cellular, wireless, etc. and as such, may be variously configured such as having one or more wired or wireless communication channels (including but not limited to: WiFi®, Bluetooth®, Near-Field Communication (NFC) and/or ANT technologies). Thus, any device within a network of FIG. 1, (such as portable electronic device 112 or any other device described herein) may be considered inclusive to one or more of the different logical networks 102-106. With the foregoing in mind, example components of an illustrative BAN and LAN (which may be coupled to WAN 106) will be described.

1. Example Local Area Network

LAN 104 may include one or more electronic devices, such as for example, computer device 114. Computer device 114, or any other component of system 100, may comprise a mobile terminal, such as a telephone, music player, tablet, netbook or any portable device. In other embodiments, computer device 114 may comprise a media player or recorder, desktop computer, server(s), a gaming console, such as for example, a Microsoft® XBOX, Sony® PlayStation, and/or a Nintendo® Wii gaming consoles. Those skilled in the art will appreciate that these are merely example devices for descriptive purposes and this disclosure is not limited to any console or computing device.

Figure 2:
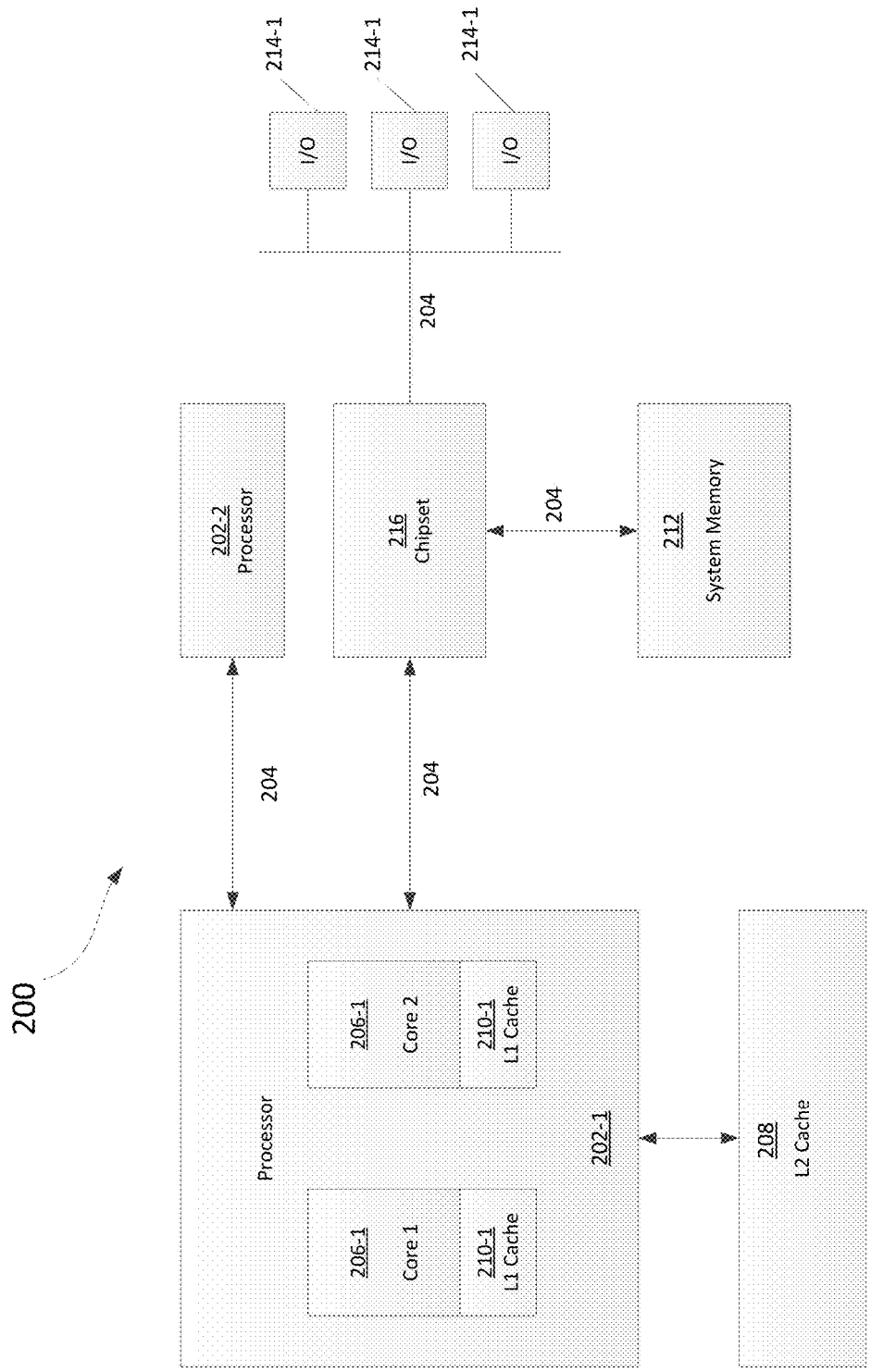
FIG. 2 illustrates an example computer device that may be part of or in communication with the system of FIG. 1.

Those skilled in the art will appreciate that the design and structure of computer device 114 may vary depending on several factors, such as its intended purpose. One example implementation of computer device 114 is provided in FIG. 2, which illustrates a block diagram of computing device 200. Those skilled in the art will appreciate that the disclosure of FIG. 2 may be applicable to any device disclosed herein. Device 200 may include one or more processors, such as processor 202-1 and 202-2 (generally referred to herein as "processors 202" or "processor 202"). Processors 202 may communicate with each other or other components via an interconnection network or bus 204. Processor 202 may include one or more processing cores, such as cores 206-1 and 206-2 (referred to herein as "cores 206" or more generally as "core 206"), which may be implemented on a single integrated circuit (IC) chip.

Cores 206 may comprise a shared cache 208 and/or a private cache (e.g., caches 210-1 and 210-2, respectively). One or more caches 208/210 may locally cache data stored in a system memory, such as memory 212, for faster access by components of the processor 202. Memory 212 may be in communication with the processors 202 via a chipset 216. Cache 208 may be part of system memory 212 in certain embodiments. Memory 212 may include, but is not limited to, random access memory (RAM), read only memory (ROM), and include one or more of solid-state memory, optical or magnetic storage, and/or any other medium that can be used to store electronic information. Yet other embodiments may omit system memory 212.

System 200 may include one or more I/O devices (e.g., I/O devices 214-1 through 214-3, each generally referred to as I/O device 214). I/O data from one or more I/O devices 214 may be stored at one or more caches 208, 210 and/or system memory 212. Each of I/O devices 214 may be permanently or temporarily configured to be in operative communication with a component of system 100 using any physical or wireless communication protocol.

Returning to FIG. 1, four example I/O devices (shown as elements 116-122) are shown as being in communication with computer device 114. Those skilled in the art will appreciate that one or more of devices 116-122 may be stand-alone devices or may be associated with another device besides computer device 114. For example, one or more I/O devices may be associated with or interact with a component of BAN 102 and/or WAN 106. I/O devices 116-122 may include, but are not limited to athletic data acquisition units, such as for example, sensors. One or more I/O devices may be configured to sense, detect, and/or measure an athletic parameter from a user, such as user 124. Examples include, but are not limited to: an accelerometer, a gyroscope, a location-determining device (e.g., GPS), light (including non-visible light) sensor, temperature sensor (including ambient temperature and/or body temperature), sleep pattern sensors, heart rate monitor, image-capturing sensor, moisture sensor, force sensor, compass, angular rate sensor, and/or combinations thereof among others.

In further embodiments, I/O devices 116-122 may be used to provide an output (e.g., audible, visual, or tactile cue) and/or receive an input, such as a user input from athlete 124. Example uses for these illustrative I/O devices are provided below, however, those skilled in the art will appreciate that such discussions are merely descriptive of some of the many options within the scope of this disclosure. Further, reference to any data acquisition unit, I/O device, or sensor is to be interpreted disclosing an embodiment that may have one or more I/O device, data acquisition unit, and/or sensor disclosed herein or known in the art (either individually or in combination).

Information from one or more devices (across one or more networks) may be used to provide (or be utilized in the formation of) a variety of different parameters, metrics or physiological characteristics including but not limited to: motion parameters, such as speed, acceleration, distance, steps taken, direction, relative movement of certain body portions or objects to others, or other motion parameters which may be expressed as angular rates, rectilinear rates or combinations thereof, physiological parameters, such as calories, heart rate, sweat detection, effort, oxygen consumed, oxygen kinetics, and other metrics which may fall within one or more categories, such as: pressure, impact forces, information regarding the athlete, such as height, weight, age, demographic information and combinations thereof.

System 100 may be configured to transmit and/or receive athletic data, including the parameters, metrics, or physiological characteristics collected within system 100 or otherwise provided to system 100. As one example, WAN 106 may comprise server 111. Server 111 may have one or more components of system 200 of FIG. 2. In one embodiment, server 111 comprises at least a processor and a memory, such as processor 206 and memory 212. Server 111 may be configured to store computer-executable instructions on a non-transitory computer-readable medium. The instructions may comprise athletic data, such as raw or processed data collected within system 100. System 100 may be configured to transmit data, such as energy expenditure points, to a social networking website or host such a site. Server 111 may be utilized to permit one or more users to access and/or compare athletic data. As such, server 111 may be configured to transmit and/or receive notifications based upon athletic data or other information.

Returning to LAN 104, computer device 114 is shown in operative communication with a display device 116, an image-capturing device 118, sensor 120 and exercise device 122, which are discussed in turn below with reference to example embodiments. In one embodiment, display device 116 may provide audio-visual cues to athlete 124 to perform a specific athletic movement. The audio-visual cues may be provided in response to computer-executable instruction executed on computer device 114 or any other device, including a device of BAN 102 and/or WAN. Display device 116 may be a touchscreen device or otherwise configured to receive a user-input.

In one embodiment, data may be obtained from image-capturing device 118 and/or other sensors, such as sensor 120, which may be used to detect (and/or measure) athletic parameters, either alone or in combination with other devices, or stored information. Image-capturing device 118 and/or sensor 120 may comprise a transceiver device. In one embodiment sensor 128 may comprise an infrared (IR), electromagnetic (EM) or acoustic transceiver. For example, image-capturing device 118, and/or sensor 120 may transmit waveforms into the environment, including towards the direction of athlete 124 and receive a "reflection" or otherwise detect alterations of those released waveforms. Those skilled in the art will readily appreciate that signals corresponding to a multitude of different data spectrums may be utilized in accordance with various embodiments. In this regard, devices 118 and/or 120 may detect waveforms emitted from external sources (e.g., not system 100). For example, devices 118 and/or 120 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology.

In one embodiment, exercise device 122 may be any device configurable to permit or facilitate the athlete 124 performing a physical movement, such as for example a treadmill, step machine, etc. There is no requirement that the device be stationary. In this regard, wireless technologies permit portable devices to be utilized, thus a bicycle or other mobile exercising device may be utilized in accordance with certain embodiments. Those skilled in the art will appreciate that equipment 122 may be or comprise an interface for receiving an electronic device containing athletic data performed remotely from computer device 114. For example, a user may use a sporting device (described below in relation to BAN 102) and upon returning home or the location of equipment 122, download athletic data into element 122 or any other device of system 100. Any I/O device disclosed herein may be configured to receive activity data.

2. Body Area Network

BAN 102 may include two or more devices configured to receive, transmit, or otherwise facilitate the collection of athletic data (including passive devices). Exemplary devices may include one or more data acquisition units, sensors, or devices known in the art or disclosed herein, including but not limited to I/O devices 116-122. Two or more components of BAN 102 may communicate directly, yet in other embodiments, communication may be conducted via a third device, which may be part of BAN 102, LAN 104, and/or WAN 106. One or more components of LAN 104 or WAN 106 may form part of BAN 102. In certain implementations, whether a device, such as portable device 112, is part of BAN 102, LAN 104, and/or WAN 106, may depend on the athlete's proximity to an access point to permit communication with mobile cellular network architecture 108 and/or WAN architecture 110. User activity and/or preference may also influence whether one or more components are utilized as part of BAN 102. Example embodiments are provided below.

User 124 may be associated with (e.g., possess, carry, wear, and/or interact with) any number of devices, such as portable device 112, shoe-mounted device 126, wrist-worn device 128 and/or a sensing location, such as sensing location 130, which may comprise a physical device or a location that is used to collect information. One or more devices 112, 126, 128, and/or 130 may not be specially designed for fitness or athletic purposes. Indeed, aspects of this disclosure relate to utilizing data from a plurality of devices, some of which are not fitness devices, to collect, detect, and/or measure athletic data. In certain embodiments, one or more devices of BAN 102 (or any other network) may comprise a fitness or sporting device that is specifically designed for a particular sporting use. As used herein, the term "sporting device" includes any physical object that may be used or implicated during a specific sport or fitness activity. Exemplary sporting devices may include, but are not limited to: golf balls, basketballs, baseballs, soccer balls, footballs, powerballs, hockey pucks, weights, bats, clubs, sticks, paddles, mats, and combinations thereof. In further embodiments, exemplary fitness devices may include objects within a sporting environment where a specific sport occurs, including the environment itself, such as a goal net, hoop, backboard, portions of a field, such as a midline, outer boundary marker, base, and combinations thereof.

In this regard, those skilled in the art will appreciate that one or more sporting devices may also be part of (or form) a structure and vice-versa, a structure may comprise one or more sporting devices or be configured to interact with a sporting device. For example, a first structure may comprise a basketball hoop and a backboard, which may be removable and replaced with a goal post. In this regard, one or more sporting devices may comprise one or more sensors, such as one or more of the sensors discussed above in relation to FIGS. 1-3, that may provide information utilized, either independently or in conjunction with other sensors, such as one or more sensors associated with one or more structures. For example, a backboard may comprise a first sensor configured to measure a force and a direction of the force by a basketball upon the backboard and the hoop may comprise a second sensor to detect a force. Similarly, a golf club may comprise a first sensor configured to detect grip attributes on the shaft and a second sensor configured to measure impact with a golf ball.

Looking to the illustrative portable device 112, it may be a multi-purpose electronic device, that for example, includes a telephone or digital music player, including an IPOD®, IPAD®, or iPhone®, brand devices available from Apple, Inc. of Cupertino, Calif. or Zune® or Microsoft® Windows devices available from Microsoft of Redmond, Wash. As known in the art, digital media players can serve as an output device, input device, and/or storage device for a computer. Device 112 may be configured as an input device for receiving raw or processed data collected from one or more devices in BAN 102, LAN 104, or WAN 106. In one or more embodiments, portable device 112 may comprise one or more components of computer device 114. For example, portable device 112 may be include a display 116, image-capturing device 118, and/or one or more data acquisition devices, such as any of the I/O devices 116-122 discussed above, with or without additional components, so as to comprise a mobile terminal.

a. Illustrative Apparel/Accessory Sensors

In certain embodiments, I/O devices may be formed within or otherwise associated with user's 124 clothing or accessories, including a watch, armband, wristband, necklace, shirt, shoe, or the like. These devices may be configured to monitor athletic movements of a user. It is to be understood that they may detect athletic movement during user's 124 interactions with computer device 114 and/or operate independently of computer device 114 (or any other device disclosed herein). For example, one or more devices in BAN 102 may be configured to function as an all-day activity monitor that measures activity regardless of the user's proximity or interactions with computer device 114. It is to be further understood that the sensory system 302 shown in FIG. 3 and the device assembly 400 shown in FIG. 4, each of which are described in the following paragraphs, are merely illustrative examples.

i. Shoe-Mounted Device

Figure 3:
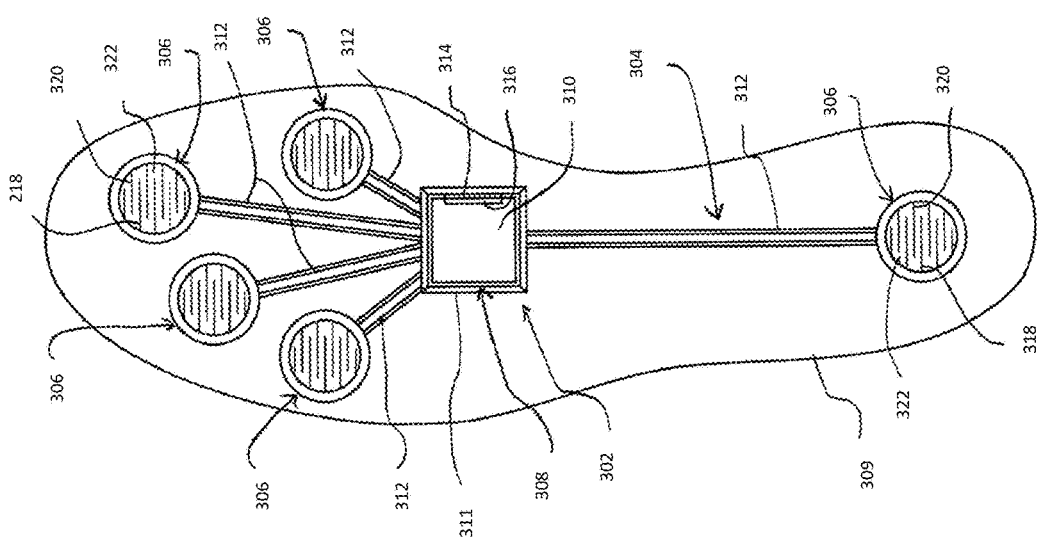
FIG. 3 shows an illustrative sensor assembly that may be worn by a user in accordance with example embodiments.

In certain embodiments, device 126 shown in FIG. 1 may comprise footwear which may include one or more sensors, including but not limited to those disclosed herein and/or known in the art. FIG. 3 illustrates one example embodiment of a sensor system 302 providing one or more sensor assemblies 304. Assembly 304 may comprise one or more sensors, such as for example, an accelerometer, gyroscope, location-determining components, force sensors and/or or any other sensor disclosed herein or known in the art. In the illustrated embodiment, assembly 304 incorporates a plurality of sensors, which may include force-sensitive resistor (FSR) sensors 306; however, other sensor(s) may be utilized. Port 308 may be positioned within a sole structure 309 of a shoe, and is generally configured for communication with one or more electronic devices. Port 308 may optionally be provided to be in communication with an electronic module 310, and the sole structure 309 may optionally include a housing 311 or other structure to receive the module 310. The sensor system 302 may also include a plurality of leads 312 connecting the FSR sensors 306 to the port 308, to enable communication with the module 310 and/or another electronic device through the port 308. Module 310 may be contained within a well or cavity in a sole structure of a shoe, and the housing 311 may be positioned within the well or cavity. In one embodiment, at least one gyroscope and at least one accelerometer are provided within a single housing, such as module 310 and/or housing 311. In at least a further embodiment, one or more sensors are provided that, when operational, are configured to provide directional information and angular rate data. The port 308 and the module 310 include complementary interfaces 314, 316 for connection and communication.

In certain embodiments, at least one force-sensitive resistor 306 shown in FIG. 3 may contain first and second electrodes or electrical contacts 318, 320 and a force-sensitive resistive material 322 disposed between the electrodes 318, 320 to electrically connect the electrodes 318, 320 together. When pressure is applied to the force-sensitive material 322, the resistivity and/or conductivity of the force-sensitive material 322 changes, which changes the electrical potential between the electrodes 318, 320. The change in resistance can be detected by the sensor system 302 to detect the force applied on the sensor 316. The force-sensitive resistive material 322 may change its resistance under pressure in a variety of ways. For example, the force-sensitive material 322 may have an internal resistance that decreases when the material is compressed. Further embodiments may utilize "volume-based resistance", which may be implemented through "smart materials." As another example, the material 322 may change the resistance by changing the degree of surface-to-surface contact, such as between two pieces of the force sensitive material 322 or between the force sensitive material 322 and one or both electrodes 318, 320. In some circumstances, this type of force-sensitive resistive behavior may be described as "contact-based resistance."

ii. Wrist-Worn Device

Figure 4:
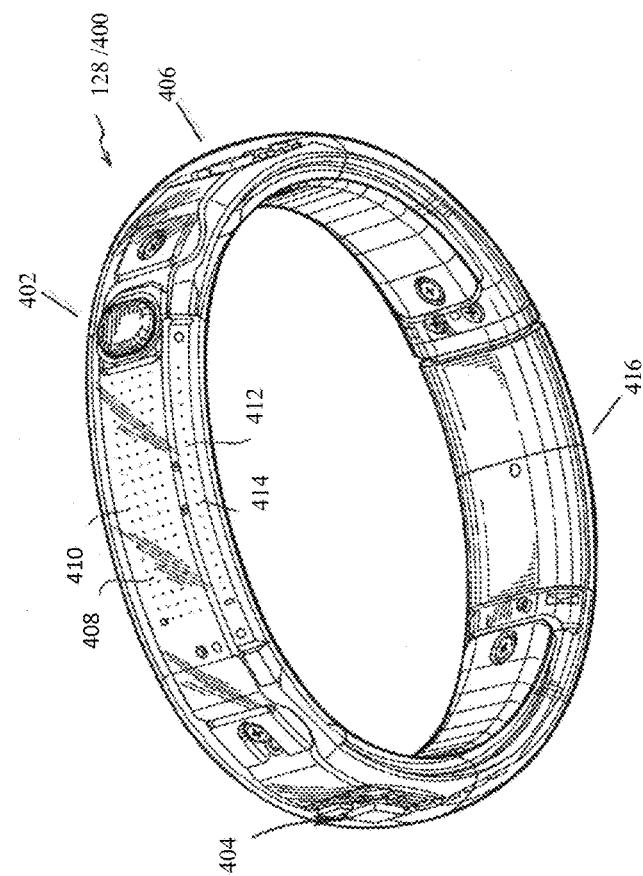
FIG. 4 shows another example sensor assembly that may be worn by a user in accordance with example embodiments.

As shown in FIG. 4, device 400 (which may resemble or comprise sensory device 128 shown in FIG. 1), may be configured to be worn by user 124, such as around a wrist, arm, ankle, neck or the like. Device 400 may include an input mechanism, such as a depressible input button 402 configured to be used during operation of the device 400. The input button 402 may be operably connected to a controller 404 and/or any other electronic components, such as one or more of the elements discussed in relation to computer device 114 shown in FIG. 1. Controller 404 may be embedded or otherwise part of housing 406. Housing 406 may be formed of one or more materials, including elastomeric components and comprise one or more displays, such as display 408. The display may be considered an illuminable portion of the device 400. The display 408 may include a series of individual lighting elements or light members such as LED lights 410. The lights may be formed in an array and operably connected to the controller 404. Device 400 may include an indicator system 412, which may also be considered a portion or component of the overall display 408. Indicator system 412 can operate and illuminate in conjunction with the display 408 (which may have pixel member 414) or completely separate from the display 408. The indicator system 412 may also include a plurality of additional lighting elements or light members, which may also take the form of LED lights in an exemplary embodiment. In certain embodiments, indicator system may provide a visual indication of goals, such as by illuminating a portion of lighting members of indicator system 412 to represent accomplishment towards one or more goals. Device 400 may be configured to display data expressed in terms of activity points or currency earned by the user based on the activity of the user, either through display 408 and/or indicator system 412.

A fastening mechanism 416 can be disengaged wherein the device 400 can be positioned around a wrist or portion of the user 124 and the fastening mechanism 416 can be subsequently placed in an engaged position. In one embodiment, fastening mechanism 416 may comprise an interface, including but not limited to a USB port, for operative interaction with computer device 114 and/or devices, such as devices 120 and/or 112. In certain embodiments, fastening member may comprise one or more magnets. In one embodiment, fastening member may be devoid of moving parts and rely entirely on magnetic forces.

In certain embodiments, device 400 may comprise a sensor assembly (not shown in FIG. 4). The sensor assembly may comprise a plurality of different sensors, including those disclosed herein and/or known in the art. In an example embodiment, the sensor assembly may comprise or permit operative connection to any sensor disclosed herein or known in the art. Device 400 and or its sensor assembly may be configured to receive data obtained from one or more external sensors.

iii. Apparel and/or Body Location Sensing

Element 130 of FIG. 1 shows an example sensory location which may be associated with a physical apparatus, such as a sensor, data acquisition unit, or other device. Yet in other embodiments, it may be a specific location of a body portion or region that is monitored, such as via an image capturing device (e.g., image capturing device 118). In certain embodiments, element 130 may comprise a sensor, such that elements 130a and 130b may be sensors integrated into apparel, such as athletic clothing. Such sensors may be placed at any desired location of the body of user 124. Sensors 130a/b may communicate (e.g., wirelessly) with one or more devices (including other sensors) of BAN 102, LAN 104, and/or WAN 106. In certain embodiments, passive sensing surfaces may reflect waveforms, such as infrared light, emitted by image-capturing device 118 and/or sensor 120. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Figure 5:
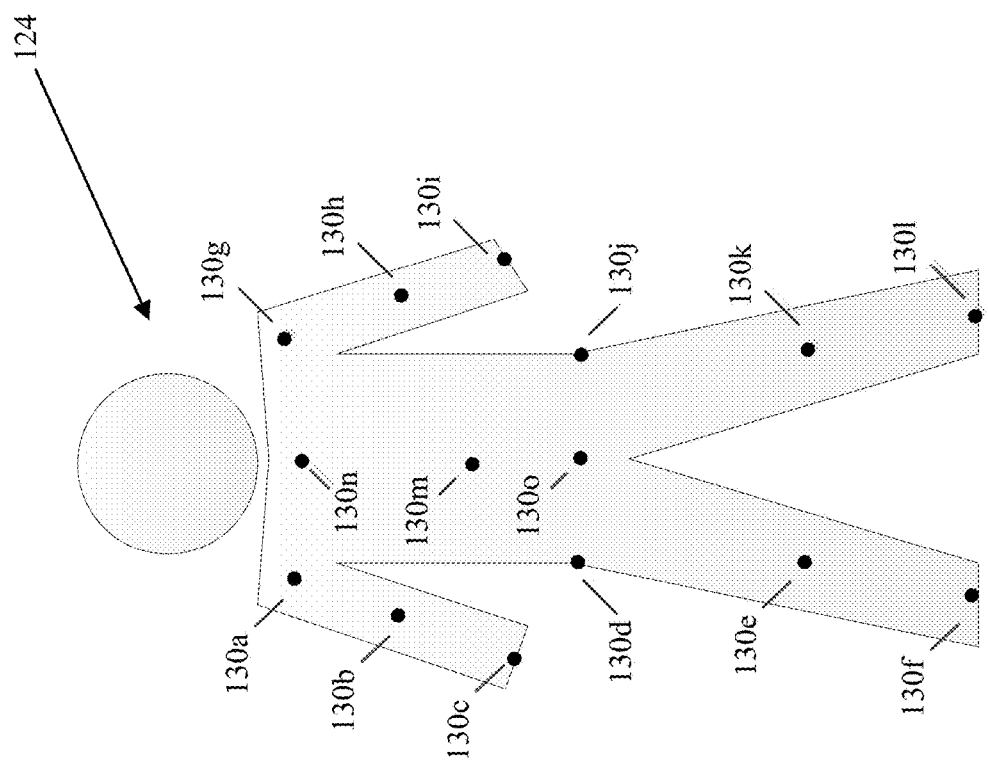
FIG. 5 shows illustrative locations for sensory input which may include physical sensors located on/in a user's clothing and/or be based upon identification of relationships between two moving body parts of the user.

FIG. 5 shows illustrative locations for sensory input (see, e.g., sensory locations 130a-130o). In this regard, sensors may be physical sensors located on/in a user's clothing, yet in other embodiments, sensor locations 130a-130o may be based upon identification of relationships between two moving body parts. For example, sensor location 130a may be determined by identifying motions of user 124 with an image-capturing device, such as image-capturing device 118. Thus, in certain embodiments, a sensor may not physically be located at a specific location (such as one or more of sensor locations 130a-130o), but is configured to sense properties of that location, such as with image-capturing device 118 or other sensor data gathered from other locations. In this regard, the overall shape or portion of a user's body may permit identification of certain body parts. Regardless of whether an image-capturing device is utilized and/or a physical sensor located on the user 124, and/or using data from other devices, (such as sensory system 302), device assembly 400 and/or any other device or sensor disclosed herein or known in the art is utilized, the sensors may sense a current location of a body part and/or track movement of the body part. In one embodiment, sensory data relating to location 130m may be utilized in a determination of the user's center of gravity (a.k.a, center of mass). For example, relationships between location 130a and location(s) 130f/130l with respect to one or more of location(s) 130m-130o may be utilized to determine if a user's center of gravity has been elevated along the vertical axis (such as during a jump) or if a user is attempting to "fake" a jump by bending and flexing their knees. In one embodiment, sensor location 1306n may be located at about the sternum of user 124. Likewise, sensor location 130o may be located approximate to the naval of user 124. In certain embodiments, data from sensor locations 130m-130o may be utilized (alone or in combination with other data) to determine the center of gravity for user 124. In further embodiments, relationships between multiple sensor locations, such as sensors 130m-130o, may be utilized in determining orientation of the user 124 and/or rotational forces, such as twisting of user's 124 torso. Further, one or more locations, such as location(s), may be utilized as (or approximate) a center of moment location. For example, in one embodiment, one or more of location(s) 130m-130o may serve as a point for a center of moment location of user 124.

In another embodiment, one or more locations may serve as a center of moment of specific body parts or regions.

Figure 6:
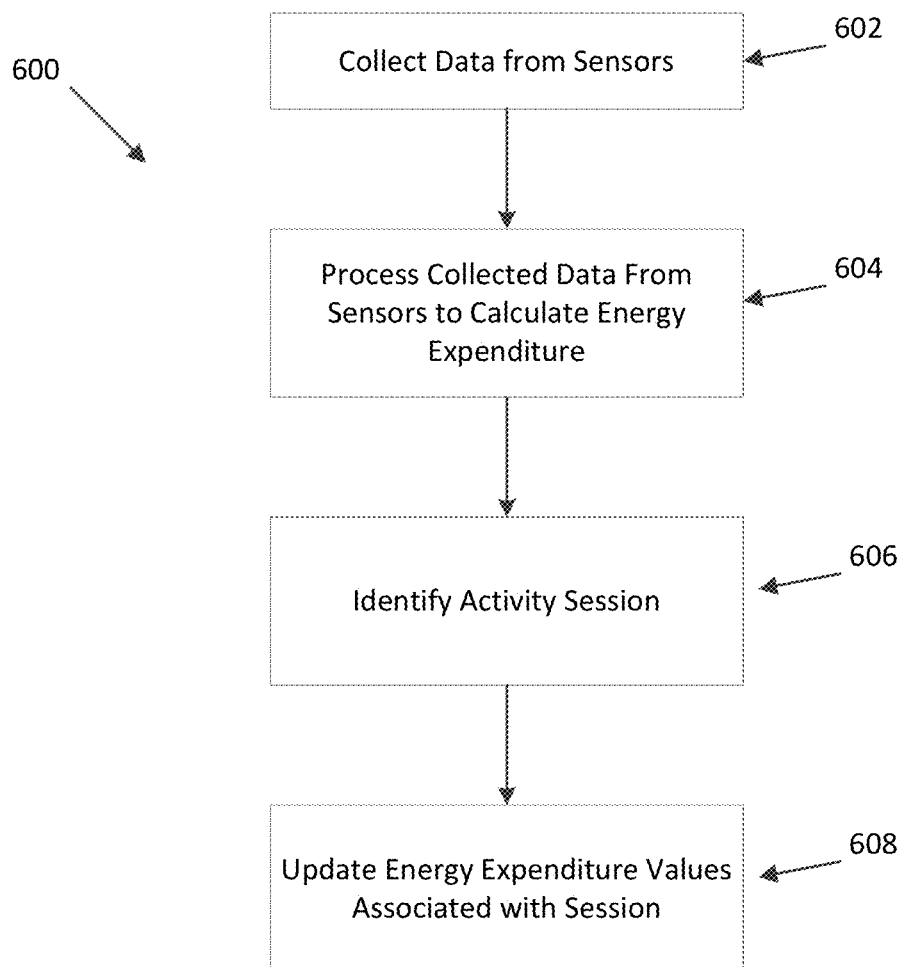
FIG. 6 schematically depicts a flowchart diagram of an activity session identification process.

FIG. 6 schematically depicts a flowchart of an example activity session identification in accordance with one embodiment. In particular, flowchart 600 may begin at block 602 with the receipt of activity data from one or more sensors associated with a device, such as devices 112, 126, 128, 130 and/or 400. Accordingly, block 602 may comprise, partially or wholly, one or more processes for receiving sensor data representative of one or more activities being carried out by a user, and as outputted by one or more sensors, including, among others, an accelerometer, a gyroscope, a location-determining device (e.g., GPS), light (including non-visible light) sensor, temperature sensor (including ambient temperature and/or body temperature), sleep pattern sensors, heart rate monitor, image-capturing sensor, moisture sensor, force sensor, compass, angular rate sensor, an RFID sensor, a wireless antenna configured to operate on one or more wired or wireless communication channels (including but not limited to: WiFi®, Bluetooth®, Near-Field Communication (NFC) and/or ANT technologies). Additionally, block 602 may include one or more processes to transform received sensor data by, among others, averaging the received sensor data, removing saturated sensor data, adjusting the received sensor data to allow for a force of gravity, performing a Fast Fourier Transform on the sensor data, among others. Furthermore, it will be apparent to those of ordinary skill in the art that various additional or alternative transformations may be performed on all or part of the received sensor data, without departing from the scope of this disclosure.

Process 600 may proceed to block 604, wherein block 604 may represent one or more processes for calculation of one or more energy expenditure values from the received sensor data. In one implementation, received sensor data may be processed to obtain an estimation of a volume of oxygen consumption by a user. Accordingly, and as will be apparent to those of ordinary skill may art, a calculated volume of oxygen consumption may be equated to an energy expenditure by the user. For example, one estimation of an energy expenditure value may equate a liter of oxygen consumption by a user to an energy expenditure value of 5 kcal, and the like. Furthermore, various systems and methods are described for calculation of one or more energy expenditure values from received sensor data in an Application No. 61/890,748 (filed Oct. 14, 2013), which is incorporated by reference in its entirety for any and all non-limiting purposes.

Block 606 of process 600 represents one or more processes to identify one or more activity sessions. In one configuration, an activity session may be a period of time during which a user carries out one or more specific and known activities. For example, an activity session may be identified as a period of time during which a user, among others, plays basketball, plays soccer, plays tennis, goes jogging, walks to work, and the like. Sessions may be automatically detected, such as by detecting movements of the user that are consistent with movement templates, processing data from one or more sensors, or other automatic mechanisms. In yet other embodiments, a user may, either before, during or after the session, manually mark the data (or a portion thereof) as belonging to a session and/or a specific type of session. Additionally or alternatively, one or more time periods during the data, such as hours of the day may be defined as activity session, or one or more half-hour periods during the day may be defined as activity sessions, and the like.

In one implementation, block 606 may execute one or more processes to identify an activity session based upon a location of the user. For example, a device, such as, among others, device 112, 126, 128, 130 and/or 400 may output sensor data from a GPS sensor indicative of a location of the user. Accordingly, an activity session may be identified based upon identified location of a user from the received GPS sensor data. For example, a tennis activity session may be identified upon receipt of GPS location sensor data identifying a current location of a user at a tennis court. In another example, a gym-workout activity session may be identified from location sensor data indicating the presence of a user as a gym, and the like. In one implementation, location sensor information may be coupled with information related to a profile of a user. For example, a dance activity session may be identified upon receipt of location information indicating the location of the user within a predetermined distance of a dance studio, and coupled with user profile information that includes information related to a subscription to a dance class at the same location, and the like. In yet further embodiments, a plurality of factors, including time, location, and/or activity data may be used to select or otherwise associate activity data with a session.

In another implementation, block 606 may represent one or more processes to identify an activity session based upon a time and/or a date. For example, an activity session may be identified based upon one or more calendar entries associated with a user, and wherein calendar information may be stored in a memory, such as system memory 212, of an activity device, such as device 112, 126, 128, 130 and/or 400, or may be stored externally to an activity device, and the like. Additionally or alternatively, an activity session may be identified at a specific time based upon a history of activity session stored in association with user activity data from an activity device. For example, a device, such as device 112, 126, 128, 130 and/or 400 may store a history of one or more activity sessions carried out by a user. Furthermore, an activity device may execute one or more processes to identify one or more trends from that stored activity session data. For example, one or more processes may recognize that a user runs 2.5 miles every Monday, Wednesday and Friday at approximately 1 PM, wherein one or more processes carried out at block 606 of process 600 may utilize prediction that the user may participate in a running activity session if a current time is approximately 1 PM on a Monday, Wednesday, or Friday.

In another embodiment, one or more activity sessions may be identified at block 606 based upon one or more additional people accompanying a user of an activity device, such as device 112, 126, 128, 130 and/or 400, and the like. For example, one or more processes may be executed to identify one or more individuals with which a user commonly plays basketball. Upon identification of one or more individuals with which the user commonly plays basketball, a basketball activity session may be identified. In another example, one or more processes may identify one or more individuals within a predetermined distance of a user, and identify the user as participating within a running race, and accordingly, identifying a race activity session.

In one implementation, one or more processes may identify one or more individuals participating in an activity with a user based upon location information provided by one or more of the individuals. For example, a user wearing an activity device, such as device 112, 126, 128, 130 and/or 400, and the like, may receive information identifying one or more individuals within a predetermined distance of the user. For example, an activity device may receive data identifying one or more individuals via a wired or wireless communication channel, and using one or more of radio frequency identification (RFID), WiFi®, Bluetooth®, Near-Field Communication (NFC) and/or ANT technologies. Additionally or alternatively, a user may receive location coordinates (in one implementation, a user may receive GPS coordinates) of one or more individuals within a predetermined range of a current location (which may come in one implementation, be identified by a GPS sensor) of a user. Furthermore, a device worn on an appendage of a user may identify communication information including a current location of said user to one or more individuals within a predetermined range of the user. Additionally, it will be readily apparent to those of skill in the art that communication between one or more individuals wearing similar or disparate sensor devices, such as devices 112, 126, 128, 130 and/or 400, may be direct, or indirect, wherein an indirect communication may be via one or more servers, and through an Internet connection, and the like.

In another embodiment, an activity session may be identified based upon contact between a pair of activity devices worn by a respective pair of users. For example, a first user may place a first activity device in temporary contact (in one example in contact for approximately one second, and the like) with a second activity device worn by a second user. Data from one or more sensors, including one or more of, among others, accelerometer data (detecting the force of contact between the devices), RFID transceiver data, and/or a near field communication (NFC) transceiver data may be used to identify contact between the first and the second activity devices, and identify an activity session based upon participation of the first and the second users.

In another implementation, block 606 of process 600 may identify one or more activity sessions associated with the user based upon one or more pieces of equipment being used by a user. For example, in activity device may identify a treadmill running activity session upon identification of a treadmill device being used by a user. For example, an activity device may identify a treadmill device based upon an RFID tag in communication with an RFID sensor associated with the activity device being worn by the user, and the like. In another example, a playing tennis activity session may be identified based upon identification of a tennis racket being used by a user, and wherein a tennis racket may be recognized based upon an RFID tag in communication with an RFID sensor associated with activity device being worn by the user, and the like.

In yet another implementation, block 606 of process 600 may identify one or more activity sessions based upon information input from a user wearing an activity device. In one example, a user may input data identifying an activity session type using a mobile device, such as a mobile phone running an application in communication with one or more activity devices being worn by the user. In another example, a user may input data identifying activity session using one or more input controls on the one or more activity devices being worn by the user. In yet another example, a user may identify (tag) one or more activity sessions as a later time, based activity sensor data saved by one or more activity devices worn by the user during the one or more activity sessions, and the like.

In one example, block 608 of process 600 may update one or more energy expenditure values associated with an activity session. As such, an energy expenditure, calculated at block 604 of process 600, may be combined with a previous energy expenditure total at block 608 to arrive at an updated energy expenditure total.

Figure 7:
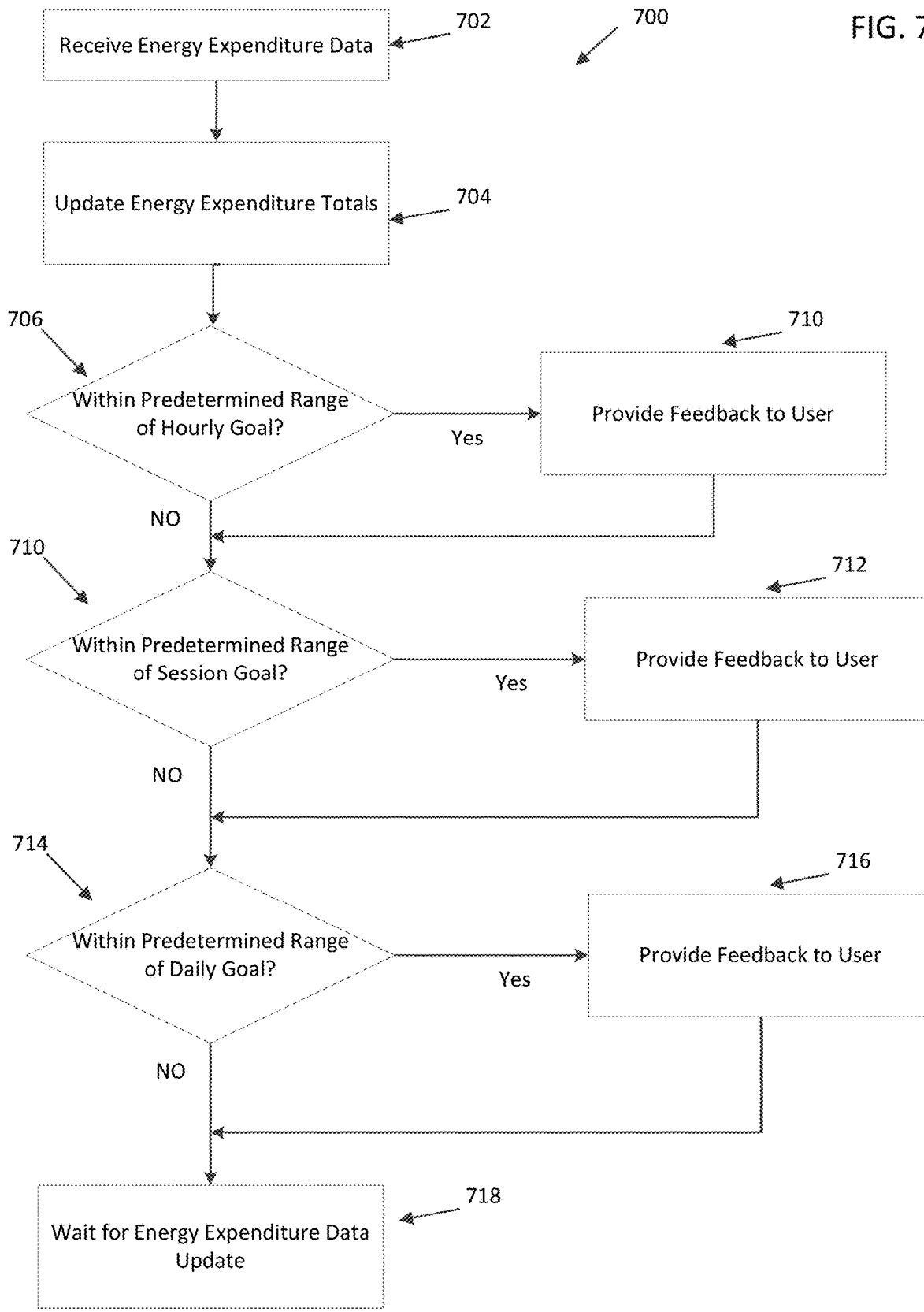
FIG. 7 depicts a flowchart diagram of a goal motivation process.

FIG. 7 depicts a flowchart of an example computer-implemented process that may be executed to provide goal motivation with respect to at least one athletic goal. In one implementation, at least a portion of goal motivation flowchart 700 may be executed by a processor, such as processor 202, of an activity device worn by a user, such as device 112, 126, 128, 130 and/or 400. In one implementation, goal motivation process 700 may provide real-time feedback to a user in response to said user being within a predetermined range of one or more goals, such as for example, an energy expenditure goal. In one implementation, flowchart 700 commences at block 702 with the receipt of energy expenditure data. In one implementation, energy expenditure data may be estimated based upon sensor data output from one or more sensors associated with an activity device worn by a user. In one example, said activity device may be worn on an appendage of a user, such as a wrist of a user, and the like. The activity device worn by a user may execute one or more processes to estimate one or more movement-related metrics, such as energy expenditure values, from sensor output data, such as accelerometer data. Those skilled in the art will appreciate that other metrics, such as for example, speed, distance, force, among others may be estimated and that other sensor data, such as data from any sensor disclosed herein and/or known in the art.

Upon receiving one or more energy expenditure values, flowchart 700 may update one or more energy expenditure totals (e.g., block 704). For example, an activity device may store in memory, such as memory 212, one or more energy expenditure totals associated with a total amount of energy expended by a user during, among others, a 24 hour period, a waking-hours period, each hour of the day, each half hour of the day, an identified activity session, and the like. In one implementation, there may be a goal energy expenditure value associated with one or more of energy expenditure totals. For example, a 24-hour period goal for a male aged approximately 30 years of age, and having a mass of approximately 80 kg may have a 24-hour period goal energy expenditure of approximately 2500 kcal, and the like.

In one embodiment, the systems and methods described herein may include one or more processes to motivate a user to achieve an energy expenditure goal based upon one or more goal strategies. In certain embodiments, the goal strategies may comprise an energy expenditure goal strategy. For example, in one implementation, a first energy expenditure goal strategy may challenge a user to expend more energy during an identified activity session than said same user expended during a prior similar activity for which information has been stored in memory, such as memory 212. Those skilled in the art will appreciate that energy expenditure is merely an example and other metrics, such as distance, pace, heart-rate, and/or other metrics may be utilized within one or more goal strategies. Thus, these and other references to energy expenditure are merely for examples and other metrics may be utilized. In another implementation, a second energy expenditure goal strategy may challenge a user to expend a predetermined amount of energy during a predetermined amount of time each day, wherein the predetermined amount of time may be each hour of the day (otherwise referred to as a "win the hour" motivation strategy). In yet another implementation, third energy expenditure goal strategy may challenge the user to exercise at or above a threshold level (which may be measured by energy expenditure, heart-rate etc.) for a minimum time span (such as 30 minutes) for a minimum quantity of times during a time frame (e.g., three times a week). In one embodiment, the threshold level may be associated with vigorous exercise, wherein vigorous exercise may be classified based upon a predetermined energy expenditure value, or percentage increase in energy expenditure above an average energy expenditure for a given user during a 30-minute period of an average week, among others.

In one implementation, upon updating one or more energy expenditure totals (e.g., at block 704), one or more of the updated energy expenditure totals may be compared against an hourly energy expenditure goal for the user (e.g. block 706). In one implementation, an hourly energy expenditure goal for a user may be a predetermined value based on one or more of an age, a height, a weight, and/or an estimation of a level of fitness of the user. In another implementation, an hourly energy expenditure goal for user may be based upon stored energy expenditure values for said user during past hours of activity. For example, in one implementation, an hourly energy expenditure goal for a user may increase by a predetermined percentage, for example 10%, during each hour of a day, and the like. In another example, an hourly energy expenditure goal for a user may vary depending upon the time of day. For example, and energy expenditure goal value may be higher for an hour during a lunchtime period, wherein it is expected up the user to exercise during his or her lunchtime hour, and the like. Block 706 may execute one or more processes to compare an energy expenditure totals for a current hour against one or more hourly energy expenditure goals. In one implementation, feedback may be provided to the user, such as via exemplary block 708. For example, if a current total energy expenditure for a current hour is within a predetermined range of an hourly goal value, feedback may be provided to the user. In one example, said predetermined range of an hourly goal value may be within 10% of an hourly goal energy expenditure value. In other implementations, however a predetermined range of an hourly goal value may be within 15%, 20%, 25%, 30%, and the like.

Block 708 of flowchart 700 may represent one or more implementations configured to provide feedback to a user to encourage said user to meet an energy expenditure goal. In one implementation, block 708 may represent one or more processes to provide a visual feedback to the user via one or more display devices associated with an activity device, such as device 112, 126, 128, 130 and/or 400, and the like. In one embodiment, the device providing the feedback is the same device comprising at least one of the sensors that detected the user's energy expenditure (and/or other metrics). For example, display 408 of device 400 may provide a visual feedback to a user to encourage the user to continue with a level of activity, or increase the level of activity in order to meet one or more energy expenditure goals during the collection of data from at least one sensor of device 400 while the user performs activity. As a further example, LED lights 410 of display 408 may display a percentage value corresponding to a fraction of a total energy expenditure by a user from a goal energy expenditure. Additionally or alternatively, LED lights 408 may display a status bar that has a fraction of a total number of LED lights 408 lit, wherein said fraction corresponds to a fraction of the total energy expenditure by a user from a goal energy expenditure value. Additionally or alternatively, LED lights 408 may be used to display a motivational message to a user to motivate the user to exercise more vigorously, or for a prolonged amount of time, and the like, to meet an energy expenditure goal. Furthermore, it will be readily understood to those of ordinary skill in the art that various other forms of visual feedback may be supplied to a user in order inform said user of a current total energy expenditure in relation to a goal energy expenditure value. In another implementation, a device, such as device 112, 126, 128, 130 and/or 400 may provide audible feedback to a user to indicate that said user is within a range of an energy expenditure goal. In one example, a speaker device may be integrated into an activity device, an output and audible signal indicative of a current total energy expenditure value as a fraction of a goal energy expenditure value. In another example, an activity device may communicate with an audio player to communicate and audible feedback message to a user. Specifically, an activity device may communicate wirelessly with, among others, a digital music player, wherein said digital music player may communication an audio message to the user via headphones or a speaker device. Additionally or alternatively, an activity device worn by the user, such as device 112, 126, 128, 130 and/or 400, may provide feedback to the user on the closeness of a current energy expenditure total to a goal energy expenditure total using haptic feedback. For example, an activity device may include a vibration motor, and provide a vibration signal upon reaching a total energy expenditure that is within a predetermined range of the goal energy expenditure, and the like.

Further embodiments may compare a total energy expenditure to one or more energy expenditure goals associated with one or more activity sessions (e.g., block 710). In one example embodiment one or more activity sessions may be identified using one or more processes described in relation to FIG. 6, and the like. In one example, block 710 may compare a total energy expenditure for a 30-minute period immediately prior to a current time against a 30-minute energy expenditure goal associated with a weekly exercise challenge. In one example, said weekly exercise challenge may encourage a user to workout vigorously three times for 30 minutes during a seven-day period, and the like. Accordingly, vigorous activity may be predetermined, and may be based upon one or more of an age, a way, a height, and/or an estimated level of fitness of a user, and the like.

In another example, block 710 may represent one or more processes to compare a total energy expenditure during a current activity session involving one or more specific individuals against a previously recorded energy expenditure value associated with a previous activity session involving said same specific individuals. For example, block 710 may compare a current total energy expenditure associated with a squash activity session between a first user and a second user to a previous squash activity session between said same first second users, and the like. Accordingly, block 710 may represent one or more processes to encourage one or more of the first user (wearing a first activity device, such as device 112, 126, 128, 130 and/or 400) and the second user (wearing a second activity device, such as device 112, 126, 128, 130 and/or 400) to meet or exceed a goal energy expenditure value associated with a squash activity session. For example, block 710 may represent one or more processes to encourage a user to increase in energy expenditure total during a squash activity session by a predetermined percentage amount over a previous energy expenditure value during a squash activity session. In one example, the predetermined percentage amount may be 10%. In another example, the predetermined percentage amount may be 15%, 20%, 25%, 30%, and the like.

Accordingly, block 710 may execute one or more processes to compare a total energy expenditure value to one or more goal energy expenditure values associated with one or more activity sessions. In one embodiment, if a total energy expenditure value for one or more activity sessions is within a predetermined range of one or more activity session goals, process 700 proceeds to block 712. Accordingly, block 712 may provide a visual, audible, and/or haptic feedback to a user to inform said user that he/she is within a predetermined range of one or more activity session energy expenditure goals. Furthermore, block 712 may provide feedback to a user in a similar manner to that described in relation to block 708.

Further aspects relate to comparing a daily energy expenditure total value against a target daily energy expenditure value (e.g., block 714). For example, a target daily energy expenditure value may be predetermined based upon one or more of an age, a weight, a height, and/or an estimated fitness level of a user. For example, a daily energy expenditure goal for a female with a height of approximately 1.62 m, a weight of approximately 55 kg, and an age of approximately 30 years, may be associated with a daily energy expenditure goal of 2000 kcal, and the like.

Block 714 may execute one or more processes to compare an energy expenditure total associated with current daily activities for a user against an energy expenditure daily goal for said user. If it is determined that the energy expenditure total for current daily activities is within a predetermined range of a daily goal energy expenditure value, process 700 may proceed to block 716. For example, block 714 may instruct process 700 to proceed to block 716 if it is determined that a total energy expenditure value for current daily activities is within 10% of a daily goal energy expenditure value, and the like.

Block 716 may represent one or more processes executed by an activity device, such as device 112, 126, 128, 130 and/or 400, to provide feedback to a user to encourage said user to undertake further physical activity to meet a daily energy expenditure goal. Accordingly, those one or more processes associated with block 760 may be a similar to those processes associated with block 712 and/or 708.

Block 718 represents one or more processes which may be executed by an activity device following processing of received energy expenditure data. Accordingly, block 718 may represent one or more processes executed by activity device to wait for new energy expenditure data updates, and the like.

Figure 8:
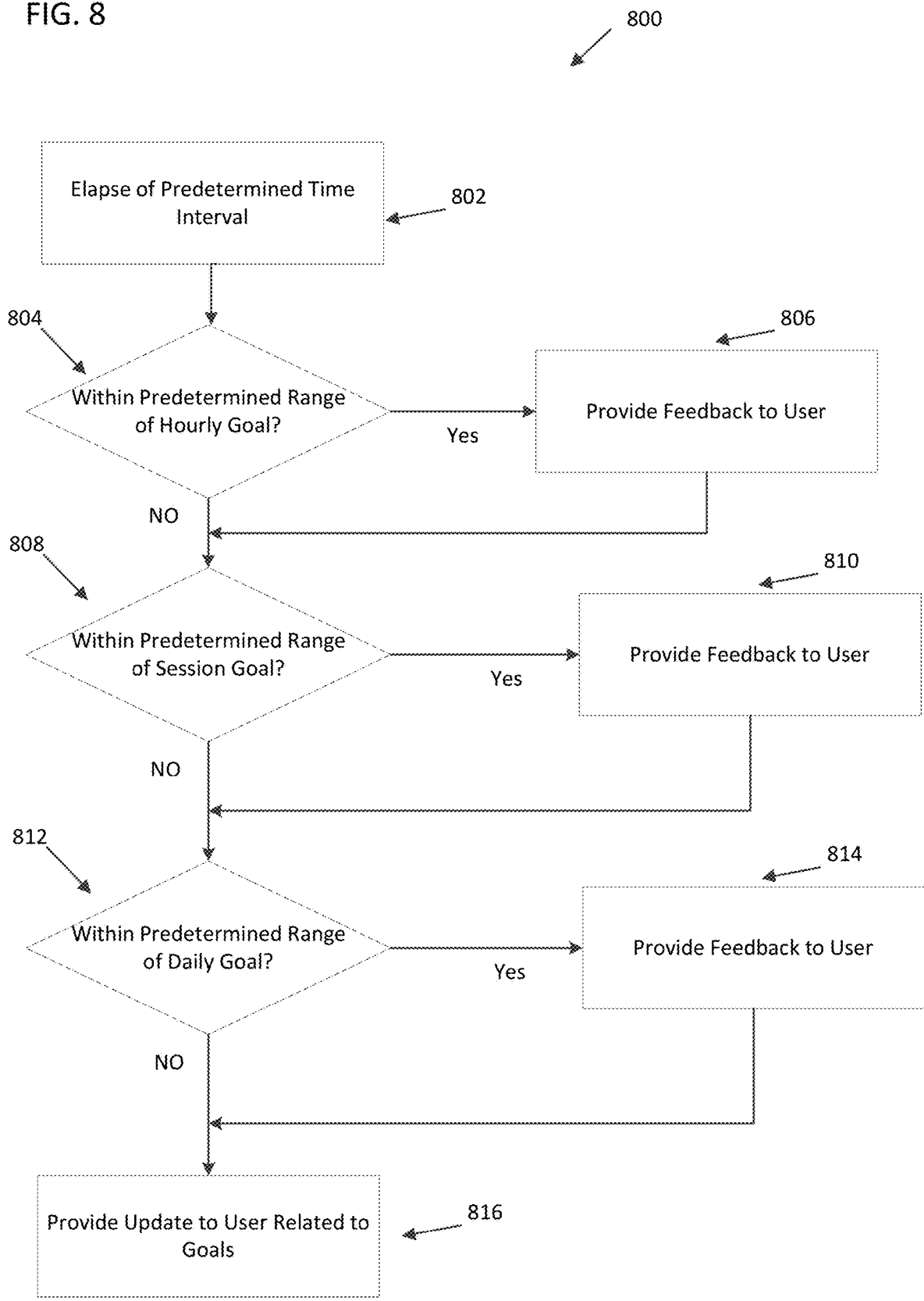
FIG. 8 depicts a flowchart diagram of an alternative goal motivation process.

FIG. 8 depicts a flowchart of another goal motivation process. In particular, flowchart 800 may provide feedback to a user based upon a closeness of one or more current energy expenditure values to one or more goal energy expenditure values. One or more portions of flowchart 800 may be executed periodically by an activity device, such as device 112, 126, 128, 130 and/or 400. Accordingly, flowchart 800 may commence at block 802 after a predetermined time interval has elapsed. In one implementation, this predetermined time interval may be based upon a level of activity indicated by one or more sensor outputs from an activity device. For example, the predetermined time interval may be longer if it is determined that activity device is not in motion, wherein a lack of motion meeting a threshold may be indicative of a lack of activity by a user, and the like. Accordingly, the predetermined time interval may range from, among others one or more milliseconds to one or more hours or longer, and the like.

Goal motivation flowchart 800 may include one or more aspects that are substantially similar to goal motivation flowchart 700 shown in FIG. 7. Accordingly, flowchart 800 may provide feedback to a user to provide encouragement to said user to continue with a level of physical activity, or increase the level of physical activity to meet one or more energy expenditure goals for, among others, each era during the day, one or more activity sessions, one or more daily activity goals, and/or one or more weekly activity goals, among others. As such, blocks 804, 806, 808, 810, 812, and 814, maybe substantially similar to blocks 706, 708, 710 from 712, 714, and 716, respectively, of process 700 from FIG. 7.

Block 816 of flowchart 800 represents an update, which may be one or more of, among others, a visual, and audible, or a haptic feedback signal to a user. Furthermore, the update associated with block 816 may provide information to a user if a user is not within a predetermined range of one or more energy expenditure goals, and the like.

We claim:

1. An apparatus, comprising:
    a processor;
    a location-determining sensor;
    an accelerometer sensor configured to output data in response to a motion of a first user; and
    a non-transitory computer-readable medium comprising computer-executable instructions, that when executed by the processor, are configured to cause the apparatus at least to:
    receive sensor data from the location-determining sensor and the accelerometer sensor;
    calculate an energy expenditure of the first user from the received sensor data;
    identify an activity session of the first user, from a plurality of activity session types, by identifying a second user, who is present within a predetermined distance of the first user, from the received sensor data, wherein the second user is identified based upon a detected force of contact between the apparatus and a device of the second user;
    calculate a total energy expenditure for the first user during the identified activity session; and
    communicate a haptic message to the first user indicating a closeness of the total energy expenditure to a goal energy expenditure.

2. The apparatus of claim 1, wherein the non-transitory computer-readable medium further comprises computer-executable instructions that, when executed by processor, are further configured to cause the apparatus at least to:
    calculate the energy expenditure of the first user based on a speed of travel of the first user as determined from location data from the location-determining sensor.

3. The apparatus of claim 1, wherein the activity session comprises an athletic activity identified based upon a location of the first user determined by the location-determining sensor.

4. The apparatus of claim 1, wherein the activity session comprises an athletic activity identified based upon a current date and time.

5. The apparatus of claim 1, wherein the activity session comprises an athletic activity identified based upon a calendar entry associated with the first user.

6. The apparatus of claim 1, wherein the activity session comprises an athletic activity identified based upon a detected proximity of the apparatus to the device of the second user.

7. The apparatus of claim 6, wherein the device of the second user comprises a piece of athletic equipment.

8. The apparatus of claim 6, wherein the second device is worn by the second user.

9. A unitary apparatus configured to be worn by a user, comprising:
    a structure configured to be worn around an appendage of a first user, comprising:

a first sensor configured to capture acceleration data from the appendage of the first user;

a second sensor configured to capture location data of the first user;

a processor, operatively connected to the first sensor, and configured to receive captured acceleration data;

a non-transitory computer-readable medium comprising computer-executable instructions that when executed by the processor cause the processor to perform at least:

receive acceleration data from the first sensor;

calculate an energy expenditure of the user from the received acceleration data;

identify an activity session of the first user, from a plurality of activity session types, by identifying a second user, who is present within a predetermined distance of the first user, from the received acceleration and location data, wherein the second user is identified based upon a detected force of contact between the unitary apparatus and a device of the second user;

calculate a total energy expenditure for the first user during the identified activity session; and communicate a message to the first user indicating a closeness of the total energy expenditure to a goal energy expenditure.

10. The unitary apparatus of claim 9, further comprising a display, wherein the message is communicated to the first user using the display.

11. The unitary apparatus of claim 9, wherein the message comprises a percentage representing the total energy expenditure as a fraction of the goal energy expenditure.

12. The unitary apparatus of claim 9, wherein the activity session is one hour in length.

13. The unitary apparatus of claim 9, wherein the activity session is one day in length.

14. The unitary apparatus of claim 9, wherein the activity session comprises a duration of a sporting activity in which the first user is participating.

15. A non-transitory computer-readable medium comprising computer-executable instructions that when executed by a processor are configured to perform at least:

receive sensor data from an activity sensor associated with a first user;

calculate an energy expenditure of the first user from the received sensor data;

identify an activity session of the first user, from a plurality of activity session types based upon a detected force of contact between the activity sensor and a second device;

calculate a total energy expenditure for the first user during the identified activity session; and communicate a message to the first user encouraging the first user to exceed a previous energy expenditure total for the identified activity session.

16. The non-transitory computer-readable medium of claim 15, wherein the message prompts the first user to exceed the previous energy expenditure total for the identified activity session by a predetermined percentage amount.

17. The non-transitory computer-readable medium of claim 15, wherein the activity sensor is an accelerometer worn on an appendage of the first user.

18. The non-transitory computer-readable medium of claim 15, wherein the activity session is identified based on an activity pattern of the received sensor data.

* * * * *